(12) United States Patent
Seemann et al.

(10) Patent No.: US 8,133,265 B2
(45) Date of Patent: Mar. 13, 2012

(54) GUIDE CATHETER, AND STENT DELIVERY SYSTEM

(75) Inventors: Michael Seemann, Munich (DE); Seiko Hamada, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1000 days.

(21) Appl. No.: 11/479,515

(22) Filed: Jun. 30, 2006

(65) Prior Publication Data

US 2008/0004685 A1      Jan. 3, 2008

(51) Int. Cl.
*A61F 2/06*          (2006.01)

(52) U.S. Cl. ..................................... 623/1.11

(58) Field of Classification Search ................. 623/1.11; 606/107, 108
See application file for complete search history.

(56) References Cited

U.S. PATENT DOCUMENTS

| | | | |
|---|---|---|---|
| 5,011,482 A * | 4/1991 | Goode et al. | 606/1 |
| 5,921,952 A | 7/1999 | Desmond, III et al. | |
| 6,478,807 B1 * | 11/2002 | Foreman et al. | 606/194 |
| 7,771,463 B2 * | 8/2010 | Ton et al. | 623/1.11 |
| 7,879,080 B2 * | 2/2011 | Sato | 623/1.11 |
| 2003/0199988 A1 * | 10/2003 | Devonec et al. | 623/23.64 |
| 2004/0220585 A1 * | 11/2004 | Nikolchev | 606/108 |
| 2005/0070821 A1 | 3/2005 | Deal et al. | |
| 2005/0085891 A1 * | 4/2005 | Goto et al. | 623/1.11 |
| 2006/0200234 A1 * | 9/2006 | Hines | 623/1.49 |
| 2006/0276873 A1 | 12/2006 | Sato | |
| 2007/0293929 A1 * | 12/2007 | Aoba et al. | 623/1.11 |
| 2009/0143849 A1 * | 6/2009 | Ozawa et al. | 623/1.11 |

FOREIGN PATENT DOCUMENTS

| | | |
|---|---|---|
| JP | 2000-152985 | 6/2000 |
| JP | 2000152985 A * | 6/2000 |
| WO | WO 2004/087006 A2 | 10/2004 |
| WO | WO 2004/110521 A2 | 12/2004 |
| WO | WO 2005/011530 A1 | 2/2005 |
| WO | WO 2006/129441 A1 | 12/2006 |

* cited by examiner

*Primary Examiner* — Gary Jackson
*Assistant Examiner* — Amy Shipley
(74) *Attorney, Agent, or Firm* — Scully, Scott, Murphy & Presser, P.C.

(57) ABSTRACT

This stent delivery system includes: a guide catheter inserted inside a stent, and inserted into the interior of the living body with the stent by a guide member inserted inside the guide catheter; a guide member inserted inside the guide catheter, and which guides the guide catheter and the stent to the interior of a living body; a pusher catheter inserted into the interior of the living body with the guide catheter in a state where the guide catheter is inserted inside the pusher catheter, and which pushes the stent along the guide catheter; and an engaging portion disposed on a head section of the guide catheter protruding from the stent, which engages with the stent in a state where the guide member is inserted into the head section, and which releases the stent in a state where the guide member is retracted away from the head section.

25 Claims, 15 Drawing Sheets

GUIDE CATHETER, AND STENT DELIVERY SYSTEM

BACKGROUND OF THE INVENTION

1. Field of the Invention

The present invention relates to a guide catheter and a stent delivery system for placing a stent into a hollow region located in the alimentary system, the respiratory system, the urinary system, the reproductive system or the like.

2. Description of the Related Art

In a case where a stricture or an obstruction arises somewhere in a hollow organ located in the alimentary system, the respiratory system, the urinary system, the reproduction system or the like, in order to restore the real function of the hollow organ, a path is ensured in the hollow organ by placing a stent into the stricture or obstruction.

Recently, the operation for placing a stent into a diseased part of the hollow organ which requires treatment is commonly performed using an endoscope and particular specific instruments. For example, in the document of U.S. Pat. No. 5,921,952, a stent delivery system used in the above-mentioned operation is disclosed. In particular, the system includes a guide catheter, a guide wire, a push catheter, and a suture for detachably connecting a stent to a tip of the push catheter. The guide catheter is inserted into the inside of the stent, and inserted into the interior of the living body with the stent. The guide wire guides the guide catheter and the stent to the interior of the living body so as to be inserted into the inside of the guide catheter. The push catheter is inserted into the interior of the living body with the guide catheter in a state where the guide catheter is inserted inside the push catheter and is used for pushing the stent along the guide catheter. Both ends of the suture are tied to each other, in a state where the suture is laced through a hole formed at a head section of the push catheter. Further, a part of the suture is inserted into the inside of the stent through a hole formed at the stent, and forms a loop. Since a head section of the guide catheter is inserted into the loop, the suture is not separated from the stent. That is, the stent is detachably connected with the tip of the push catheter through the suture.

With the operation, first, the four members are joined as mentioned above, that is, the stent, the guide catheter, the push catheter and the suture are inserted into a channel of an endoscope along the guide wire, then the members are protruded from a tip of an insertion portion of the endoscope. The stent and the head section of the guide catheter are inserted into an affected part of a hollow organ which requires a procedure.

Next, in a state where the guide wire and the push catheter are held in place, the guide catheter is retracted by being pulled from the channel of the insertion portion of the endoscope. At this time, it is not always necessary to retract the entire guide catheter. When the guide catheter is pulled, the head section of the guide catheter is retracted away from the loop of the suture, accordingly the constraint of the stent by the guide catheter is removed. Next, in the same way as the guide catheter, the guide wire is retracted by being pulled so as to be retracted from the channel of the insertion portion of the endoscope. At this time, also it is not always necessary to retract the entire guide wire. When the guide wire is pulled, the tip of the guide wire is retracted away from the loop of the suture, and accordingly the constraint of the stent by the guide catheter is removed. As a result, the engagement between the stent and the push catheter through the suture is released.

Next, when the push catheter is pulled so as to be retracted from the channel of the insertion portion of the endoscope, since the engagement between the stent and the push catheter has been separated already, only the stent is placed at the affected part of a hollow organ which requires a procedure.

With the operation as mentioned above, when the stent and the head section of the guide catheter are inserted into the affected part of a hollow organ which requires a procedure, if the stent is placed at a position which is deeper than the affected part, the push catheter is pulled slightly before pulling the guide catheter or the guide wire, that is, before separating the engagement between the stent and the push catheter. Therefore, it is possible to replace the stent connected with the tip of the push catheter to the desired position.

SUMMARY OF THE INVENTION

The present invention is a guide catheter inserted inside a stent and inside a pusher catheter which pushes the stent, and inserted into the interior of a living body with the stent and the pusher catheter by being guided along a guide member inserted inside the catheter, wherein an engaging portion which engages with the stent in a state where the guide member is inserted into a head section of the guide catheter protruding from the stent, and which releases the stent in a state where the guide member is retracted away from the head section is provided on the head section.

The guide catheter of the present invention may be arranged such that the engaging portion is supported by the guide member so as to protrude outward, and thereby engages with the stent in the state where the guide member is inserted into the head section of the guide catheter, and it may be arranged such that the engaging portion goes back to an initial position by losing the support of the guide member, and thereby releases the stent in the state where the guide member is retracted away from the head section.

The guide catheter of the present invention may be arranged such that the engaging portion is supported by the guide member so as not to move inward, and thereby engages with the stent in a state where the guide member is inserted into the head section of the guide catheter, and it may be arranged such that the engaging portion loses the support of the guide member, and thereby becomes movable inward in a state where the guide member is retracted away from the head section.

The guide catheter of the present invention may be arranged such that the engaging portion is provided on the inside surface of a tube wall of the guide catheter so as to protrude toward the inside of the guide catheter. Also, it may be arranged such that the engaging portion is provided on the outside surface of a tube wall of the guide catheter so as to protrude toward the outside of the guide catheter.

The guide catheter of the present invention may be arranged such that the engaging portion is a thickness portion integrally-formed with a tube wall of the guide catheter. Also, it may be arranged such that the engaging portion is another member fixed to a tube wall of the guide catheter.

The guide catheter of the present invention may be arranged such that a notch which makes the engaging portion move easily is formed in the head section of the guide catheter.

The stent delivery system of the present invention is for placing a cylindrically-shaped stent at a desired position within a living body, including: a guide catheter inserted inside the stent, and inserted into the interior of the living body with the stent by a guide member inserted inside the guide catheter; a pusher catheter formed like a tube shape, and inserted into the interior of the living body with the guide catheter in a state where the guide catheter is inserted to the inside the pusher catheter, and which is for pushing the stent along the guide catheter; and an engaging portion disposed on a head section of the guide catheter protruding from the stent, which engages with the stent in a state where the guide member is inserted into the head section, and which releases the stent in a state where the guide member is retracted away from the head section.

The stent delivery system of the present invention may be arranged such that the engaging portion is supported by the guide member so as to protrude outward, and thereby engages with the stent in the state where the guide member is inserted into the head section of the guide catheter, and it may be arranged such that the engaging portion goes back to an initial position by losing the support of the guide member, and thereby releases the stent in the state where the guide member is retracted away from the head section.

The stent delivery system of the present invention may be arranged such that the engaging portion is supported by the guide member so as not to move inward, and thereby engages with the stent in the state where the guide member is inserted into the head section of the guide catheter, and it may be arranged such that the engaging portion loses the support of the guide member, and thereby becomes movable inward in the state where the guide member is retracted away from the head section.

The stent delivery system of the present invention may be arranged such that the engaging portion is provided on the inside surface of a tube wall of the guide catheter so as to protrude toward the inside of the guide catheter. Also, it may be arranged such that the engaging portion is provided on the outside surface of a tube wall of the guide catheter so as to protrude toward the outside of the guide catheter.

The stent delivery system of the present invention may be arranged such that the engaging portion is a thickness portion integrally-formed with a tube wall of the guide catheter. Also, it may be arranged such that the engaging portion is another member fixed to a tube wall of the guide catheter.

The stent delivery system of the present invention may be arranged such that a notch which makes the engaging portion move easily is formed in the head section of the guide catheter.

The stent delivery system of the present invention may be arranged such that a projection is formed on the inside surface of the stent, and the engaging portion constrains the stent by engaging with the projection.

The stent delivery system of the present invention may be arranged such that the stent and the pusher catheter engage with a part in which the guide member of the guide catheter is inserted, in the state where the guide member is inserted into the head section of the guide catheter.

DESCRIPTION OF THE PREFERRED EMBODIMENTS

A description is given of a first embodiment of the stent delivery system of the present invention with reference to FIG. 1 through FIG. 9.

Figure 1:
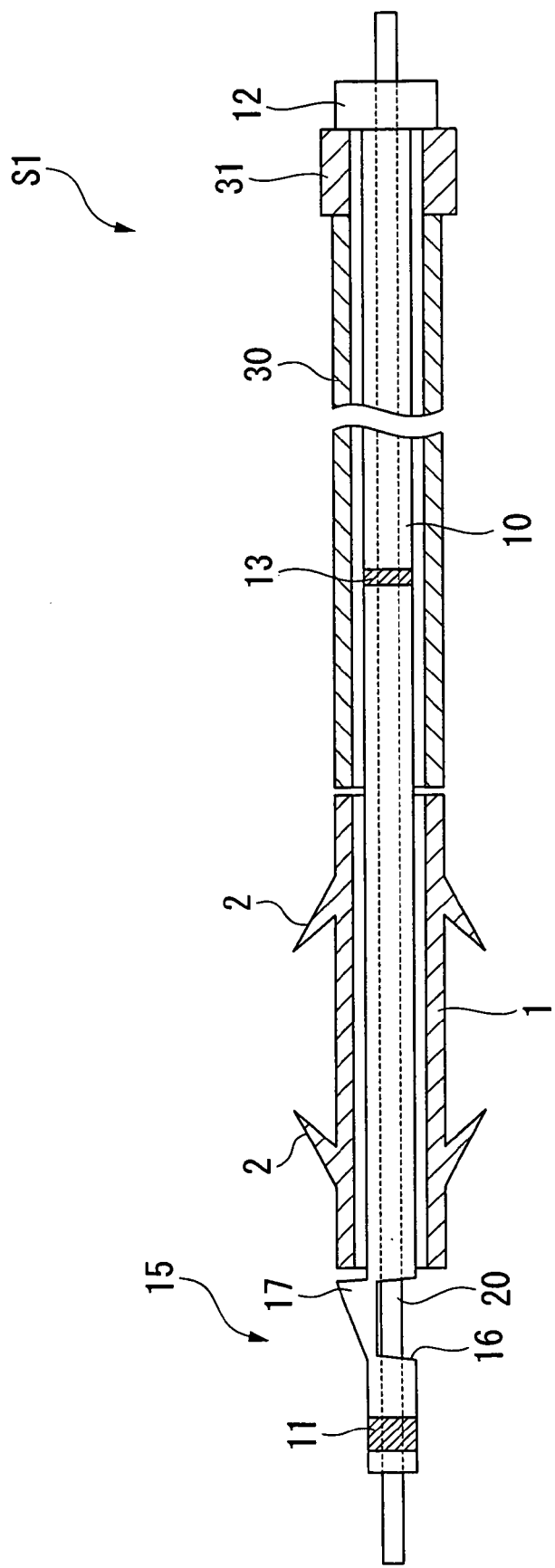
FIG. 1 is a sectional view showing a first embodiment of a stent delivery system of the present invention.

As shown in FIG. 1, a stent delivery system S1 of this embodiment includes a guide catheter 10 and a pusher catheter 30.

The guide catheter 10 is inserted inside a stent 1, and is inserted into the interior of the living body with the stent 1 through a channel formed within an insertion portion of an endoscope by being guided along a guide wire (guide member) 20 previously-inserted into a target position. The pusher catheter 30 is inserted to the interior of the living body with the guide catheter 10 in a state where the guide catheter 10 is inserted inside the pusher catheter 30, and pushes the stent 1 along the guide catheter 10.

The stent 1 is made of resin or metal, and is formed like a cylinder, and is placed inside the interior of the living body by the stent delivery system S1. Flaps 2 are formed in both ends of the stent 1. When the stent 1 is inserted into a stricture within the living body, the flaps 2 act as anchors for holding the stent 1 itself in place.

The guide catheter 10 is made of resin, and is formed like a flexible and long tube. The internal diameter of the guide catheter 10 is a predetermined size so that a guide wire 20 can be detachably inserted inside the guide catheter 10.

A contrasting portion 11 for easily improving the contrast of a head section of the guide catheter 10 under X-ray illumination is disposed at the head section of the guide catheter 10. A sleeve 12 grasped by an operator when the guide catheter 10 is operated is disposed at the base end of the guide catheter 10. Further, indicators 13 are disposed on the outside surface of a part of the guide catheter 10 which is close to the sleeve 12. The indicators 13 are used for allowing the operator to recognize the length of the guide catheter 10 pulled by highlighting the position of the guide catheter 10 with respect to the pusher catheter 30.

Further, an engaging portion 15 is disposed on the head section of the guide catheter 10. The engaging portion 15 engages with the stent 1 in a state where the guide wire 20 is inserted into the head section of the guide catheter 10, and releases the stent 1 in a state where the guide wire 20 is retracted away from the head section.

Figure 2:
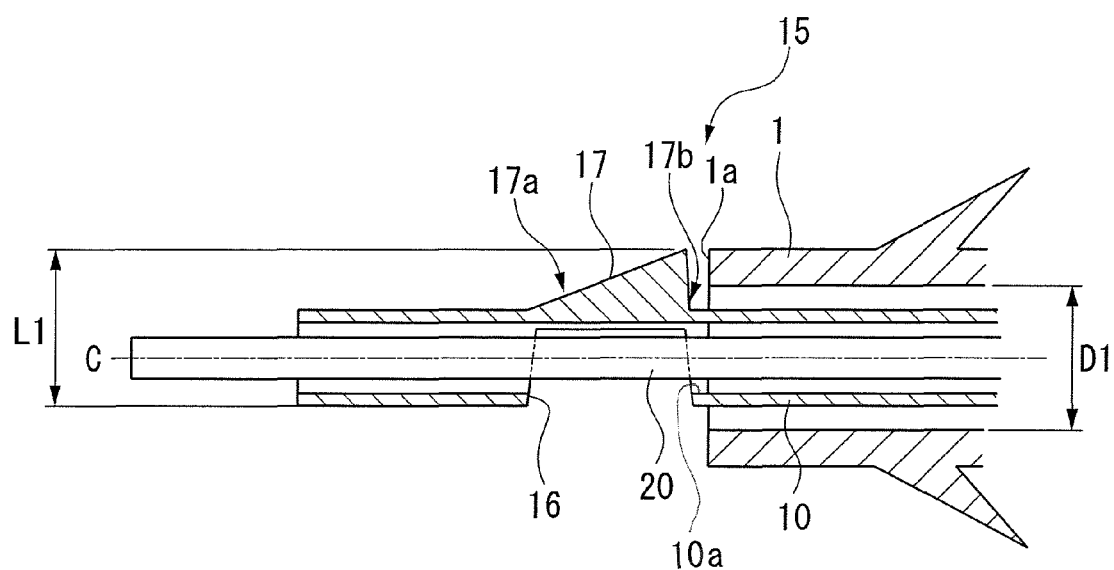
FIG. 2 is a sectional view showing the head section of the guide catheter included in the stent delivery system of the first embodiment.

The engaging portion 15 includes a cutout 16 formed in a part of a tube wall of the guide catheter 10, and a projection 17 which protrudes outward along the radius of the guide catheter 10 from the tube wall in which the cutout 16 is formed. The cutout 16 communicates with a tube hole 10a of the guide catheter 10. As shown in FIG. 2, the projection 17 is integrally-formed with the guide catheter 10, and includes an inclined surface 17a which inclines toward a tip of the guide catheter 10, and an inclined surface 17b which inclines toward a terminal of the guide catheter 10. The inclined surface 17b has a steeper incline than the inclined surface 17a. Further, a distance L1 from a top of the projection 17 to the outside surface of the guide catheter 10 positioned at the opposite side of the projection 17 across a center axis C of the guide catheter 10 is longer than the internal diameter D1 of the stent 1.

In a state where the guide wire 20 is inserted inside the guide catheter 10, the guide wire 20 is exposed by the cutout 16. Further, in this state, the guide wire 20 inserted inside the guide catheter 10 supports the projection 17 from the inside of the guide catheter 10, and thereby the projection 17 is prevented from moving inward along the radius of the guide catheter 10. On the other hand, in a state where the guide wire 20 is retracted away from the guide catheter 10, the projection 17 can move inward along the radius of the guide catheter 10, because the projection 17 loses the support of the guide wire 20.

The guide wire 20 is made of resin or metal, and is inserted inside the guide catheter 10.

The pusher catheter 30 is made of resin, and is formed like a flexible and long tube similar to the guide catheter 10. The internal diameter of the pusher catheter 30 is a predetermined size so that the guide catheter 10 can be detachably inserted inside the pusher catheter 3,0. A sleeve 31 grasped by an operator when the pusher catheter 30 is operated is disposed at the base end of the pusher catheter 30.

The stent 1 and the pusher catheter 30 are engaged with the guide catheter 10 in a state where the guide wire 20 is inserted into the head section of the guide catheter 10.

A description is given of a procedure of an operation for placing the stent at a stricture of the biliary tract using the stent delivery system SI constructed as mentioned above.

In the operation, first, an insertion portion 6 of an endoscope is inserted into the interior of a living body, then a tip of the insertion portion 6 reaches the vicinity of a duodenal papilla A. Note that a lateral vision type endoscope is used with this operation. A standing block 8 is disposed at the tip of the insertion portion 6 of the endoscope so as to be close to an opening of a channel 7 (see FIG. 3). The standing block 8 makes an instrument protruding from the tip of the insertion portion 6 curve so as to adjust the protruding angle of the instrument. The standing block 8 is moved by operating an operation section (not illustrated) disposed at a base end of the endoscope.

Figure 4:
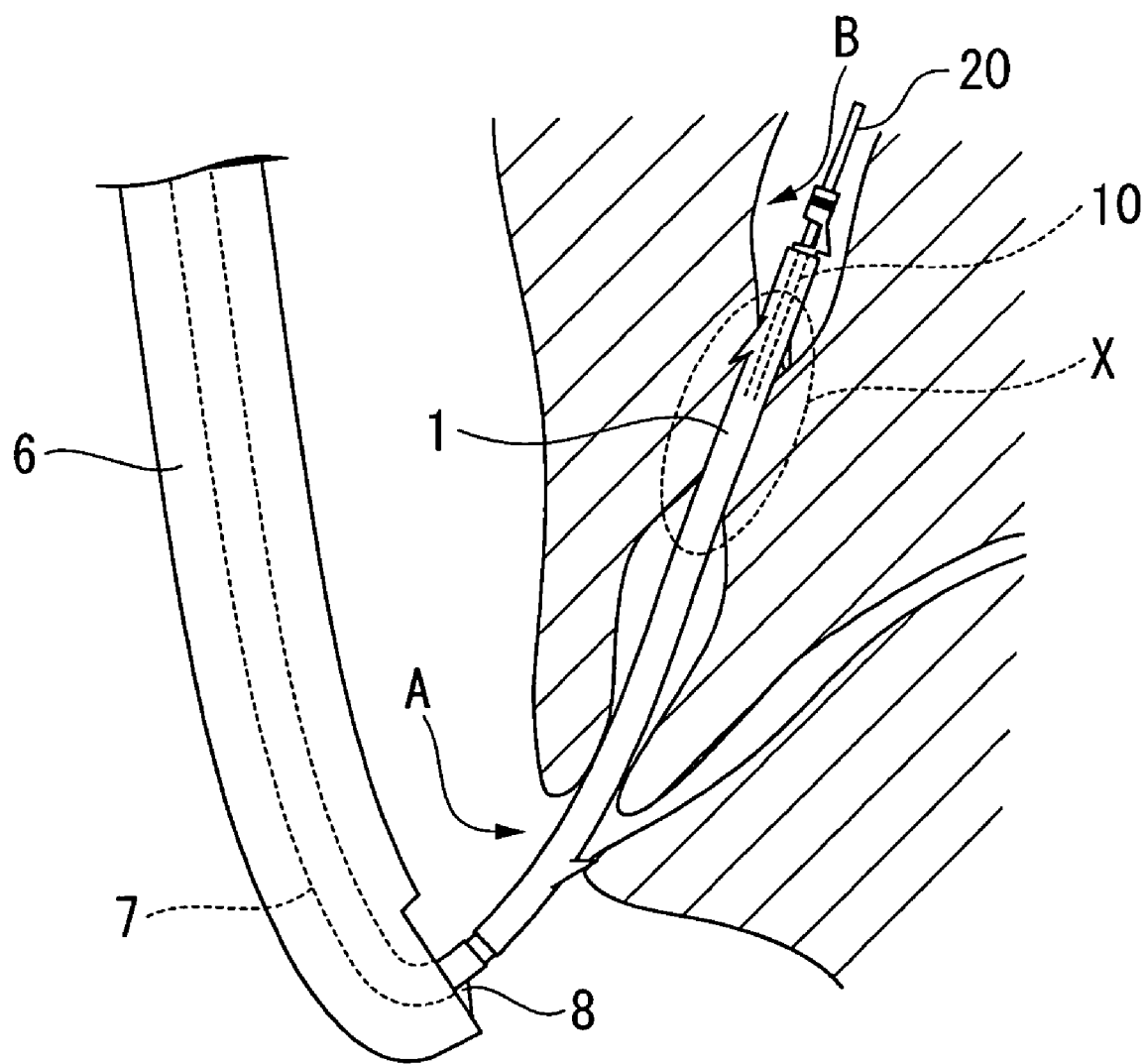
FIG. 4 is a view for depicting the procedure of the operation performed using the stent delivery system of the first embodiment, and shows a state where the stent and the guide catheter are inserted into the stricture.

Next, a cannula is inserted into the channel 7 of the insertion portion 6, then the cannula is protruded from the tip of the insertion portion 6. The cannula is curved by the standing block 8, then a head section of the cannula is inserted into a biliary tract B. A contrast agent is introduced into the biliary tract B through the cannula. After introducing the contrast agent, the guide wire 20 is inserted into a stricture X of the biliary tract B through the cannula. Thereafter, as shown in FIG. 4, the cannula is retracted away from the biliary tract B and the channel 7 while leaving only the guide wire 20.

Next, the three members joined as shown in FIG. 1, that is, the stent 1, the guide catheter 10, and the pusher catheter 30, are inserted into the channel 7 along the guide wire 20, then the members are protruded from the tip of a insertion portion 6. The guide catheter 10, the guide wire 20 and the pusher catheter 30 are curved by the standing block 8, as shown in FIG. 4, and the stent 1 and the head section of the guide catheter 10 are inserted into the stricture X.

Figure 3:
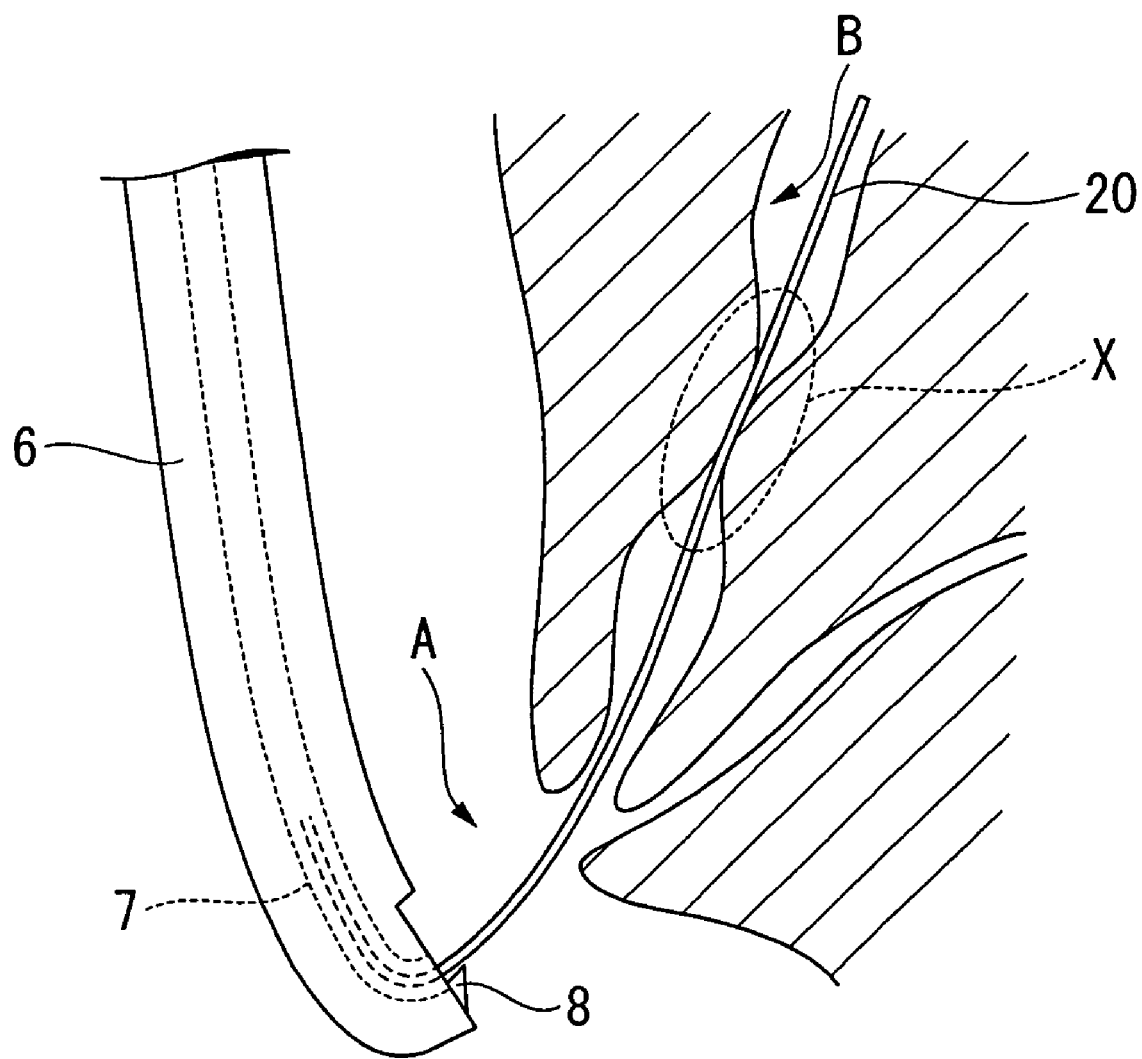
FIG. 3 is a view for depicting the procedure of the operation performed using the stent delivery system of the first embodiment, and shows a state where the head section of the insertion portion of the endoscope is disposed in the vicinity of the duodenal papilla, and the guide wire is inserted into the stricture of the biliary tract.
Figure 6:
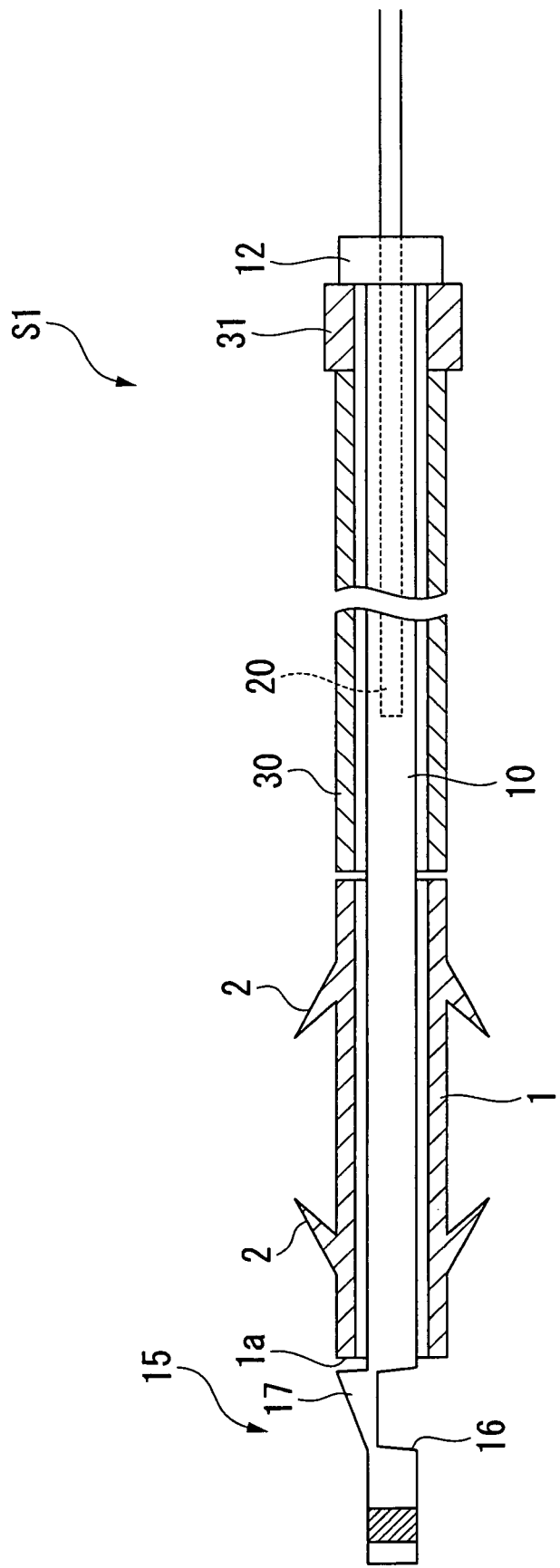
FIG. 6 is a view for depicting the procedure of the operation performed using the stent delivery system of the first embodiment, and shows a state where the guide wire is retracted.

Next, as shown in FIG. 6, in a state where the pusher catheter 30 is held in place, the guide wire 20 is retracted by pulling so as to be retracted from the channel 7 of the insertion portion 6 of the endoscope(see FIG. 3). At this time, it is not always necessary to retract the full length of the guide wire 20. When the guide wire 20 is pulled, the tip end section of the guide wire 20 is retracted away from the stent 1, and retracts to the inside of the pusher catheter 30. When the tip end section of the guide wire 20 is retracted to the inside of the pusher catheter 30, the projection 17 can move inward along the radius of the guide catheter 10 because the guide wire 20 supporting the projection 17 from the inside of the guide catheter 10 is left.

Figure 7:
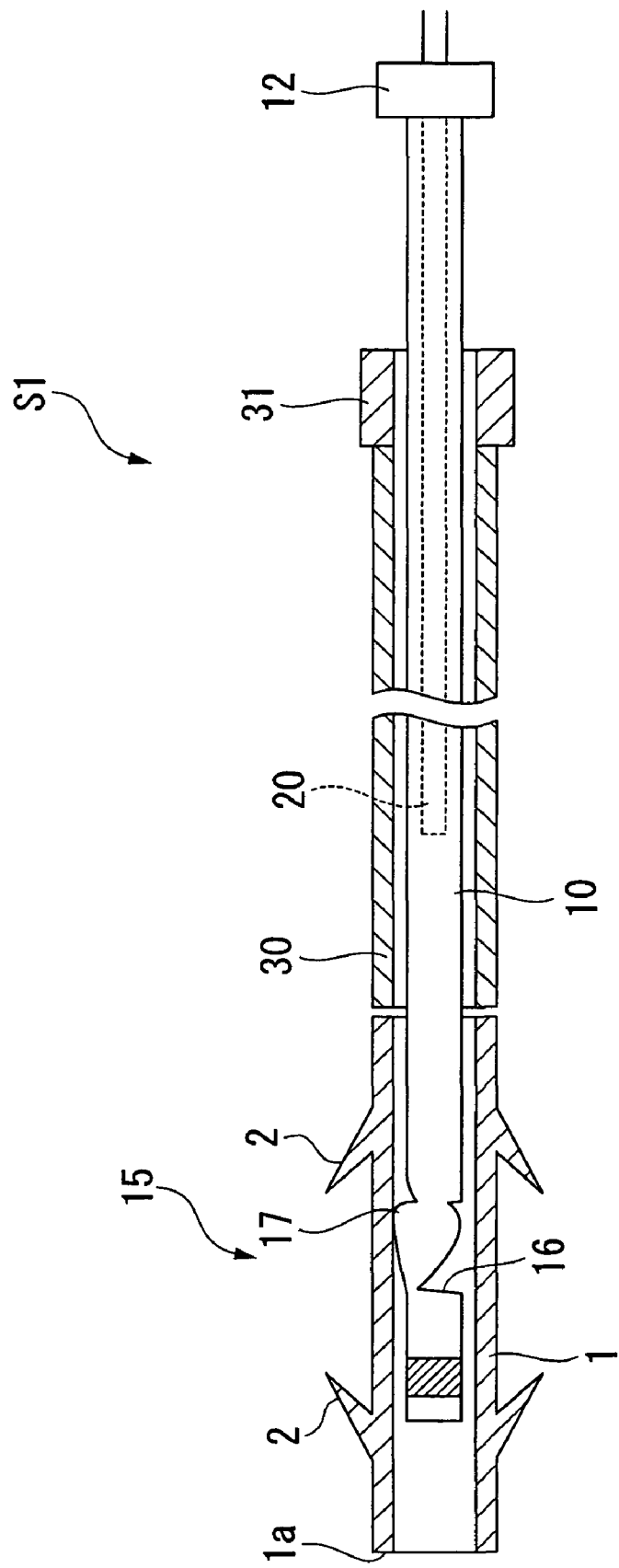
FIG. 7 is a view for depicting the procedure of the operation performed using the stent delivery system of the first embodiment, and shows a state where the guide catheter is in the middle of being retracted.

Next, as shown in FIG. 7, in a state where the pusher catheter 30 is held in place, the guide catheter 10 is retracted by pulling the guide catheter 10 so as to retract it away from the channel 7 of the insertion portion 6 of the endoscope(see FIG 3). At this time, it is not always necessary to retract the full length of the guide catheter 10. The operator may cause relative movement of the guide catheter 10 relative to the pusher catheter 30 using an indicator 13 as a target. When the guide catheter 10 is pulled, the projection 17 contacts an end surface of the stent 1. In a state where the tip of the guide wire 20 protrudes from the tip of the guide catheter 10, the guide wire 20 supports the projection 17 from the inside of the guide catheter 10, and thereby the projection 17 is prevented from moving inward in the radius direction of the guide catheter 10. However, since the tip end section of the guide wire 20 is already retracted to the inside of the pusher catheter 30, when the guide catheter 10 is pulled, the projection 17 moves inward along the radius of the guide catheter 10 by means of a reaction force acting from the end surface 1a of the stent 1.

Figure 8:
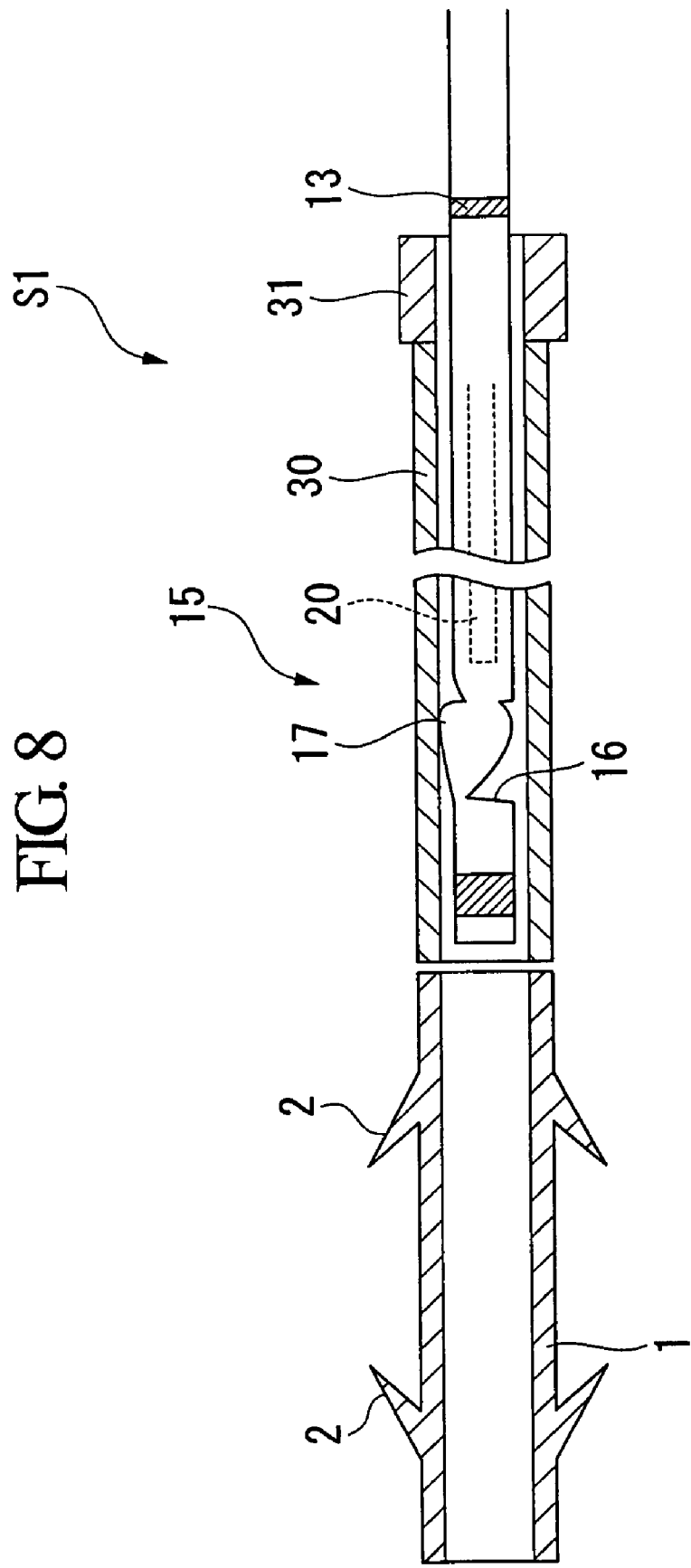
FIG. 8 is a view for depicting the procedure of the operation performed using the stent delivery system of the first embodiment, and shows a state where the head section of the guide catheter is retracted to the inside of the pusher catheter.

When the projection 17 moves to the inside of the guide catheter 10, the engaging portion 15 releases the stent 1. When the guide catheter 10 is pulled until the indicator 13 becomes exposed at the sleeve 31, as shown in FIG. 8, the head section of the guide catheter 10 is retracted away from the stent 1, and then retracts to the inside of the pusher catheter 30.

Figure 5:
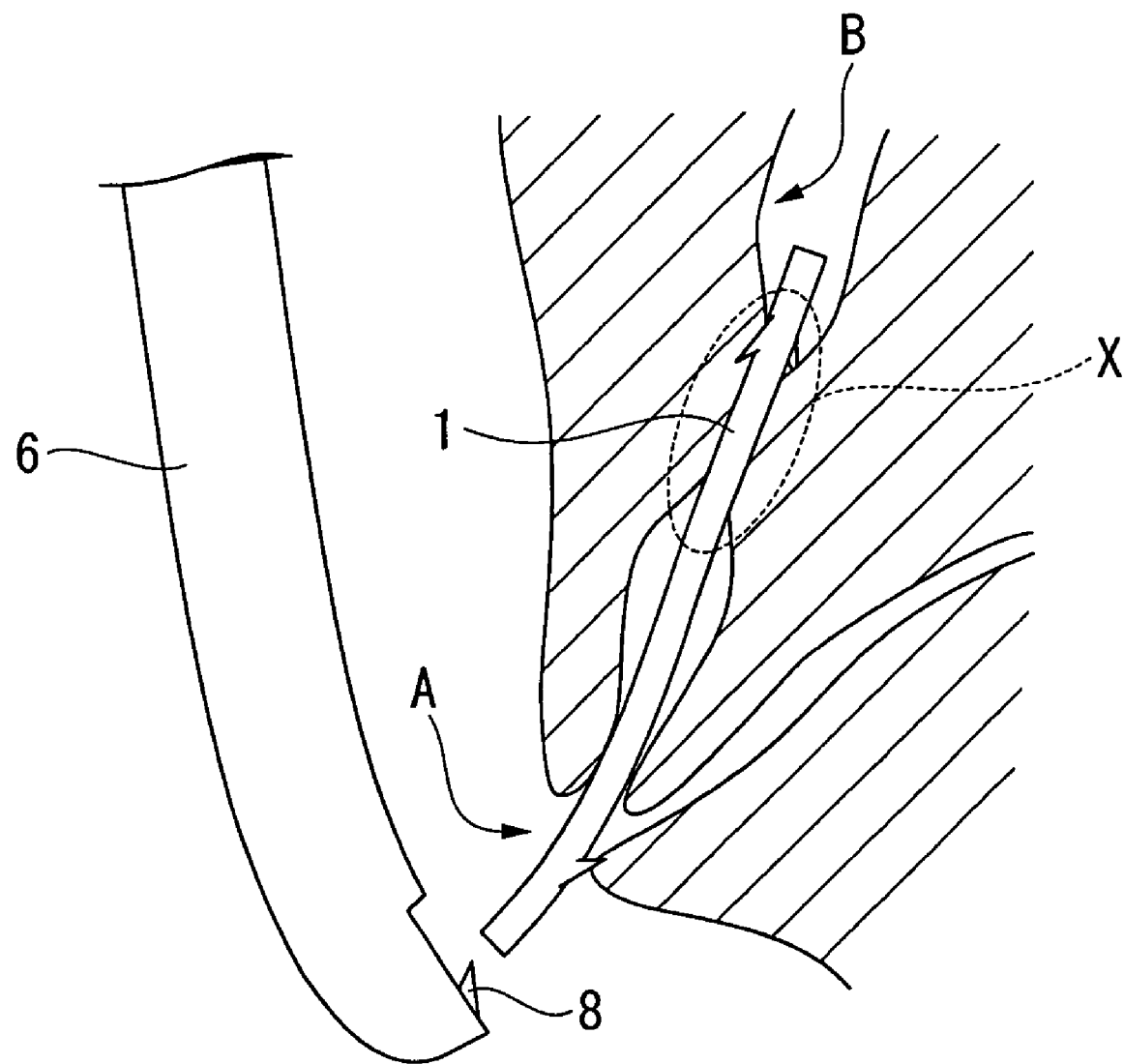
FIG. 5 is a view for depicting the procedure of the operation performed using the stent delivery system of the first embodiment, and shows a state where only the stent is placed at the stricture.

Next, when the pusher catheter 30 is retracted by pulling so as to be retract from the channel 7 of the insertion portion 6 of the endoscope (see FIG 3), as shown in FIG. 5, finally, only the stent 1 is placed at the interior of the biliary tract B.

With the operation as mentioned above, when the stent 1 and the head section of the guide catheter 10 are inserted into the stricture X, if the stent 1 is placed at a position which is deeper than the target position, the operator pulls the guide catheter 10 and the pusher catheter 30 slightly before the guide wire 20 is retracted. Therefore, it is possible to replace the stent 1 connected to the tip of the pusher catheter 30 to the desired position.

According to the stent delivery system S1 constructed as mentioned above, the engaging portion 15 provided with the guide catheter 10 engages with the stent 1 at the tip of the pusher catheter 30. As a result, if the stent 1 is placed at a position which is deeper than the target position, it is possible to replace the stent 1 at the accurate position.

With the stent delivery system S1, it is not necessary to insert special instruments inside the guide catheter 10 and the pusher catheter 30, and the basic construction of the system is substantially equal to the conventional stent delivery system. Therefore, it is possible to apply the stent delivery system S1 to the endoscope used with the conventional stent delivery system. That is, it is possible to insert the system into the channel, the internal diameter of which is equal to that of a channel of the endoscope used with the conventional stent delivery system.

With the stent delivery system S1, it is possible to use a ready-made stent in the procedure. Further, if the internal diameter of the stent 1 is in conformity with the external diameter of the guide catheter 10, and the external diameter thereof is in conformity with the external diameter of the pusher catheter 30, any stent in which the material, the length, and the shape of the flap are different from the stent 1 as mentioned above may be used. That is, the system can be used widely. In addition, the operator can attach any stent having a shape and material suitable for treatment to the stent delivery system and perform the procedure using the system.

Figure 9:
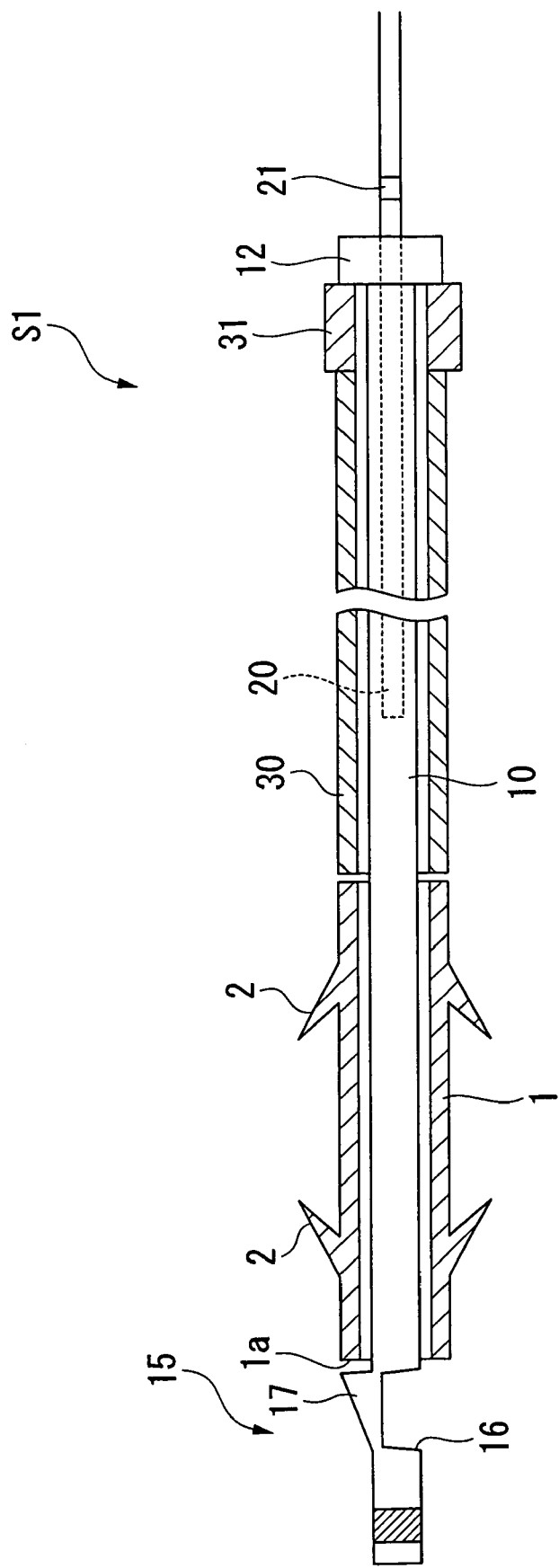
FIG. 9 is a sectional view showing a variant relating to the first embodiment of the stent delivery system of the present invention.

With this embodiment, as shown in FIG. 9, an indicator 21 may be disposed on the outside surface of a part of the guide wire 20. The indicator 21 is used for allowing the operator to recognize the length of the guide catheter 10 pulled by highlighting the position of the guide wire 20 with respect to the guide catheter 10. In this case, the operator causes relative movement of the guide wire 20 relative to the guide catheter 10 using an indicator 21 as a target. When the guide wire 20 is pulled until the indicator 21 becomes exposed at the sleeve 12, the tip end section of the guide wire 20 is retracted away from the stent 1, and then retracts to the inside of the pusher catheter 30 reliably.

A description is given of a second embodiment of the stent delivery system of the present invention with reference to FIG. 10 through FIG. 16. Note that the same descriptive symbols are used for component elements that are the same as those used in the first embodiment and the descriptions thereof are omitted.

Figure 10:
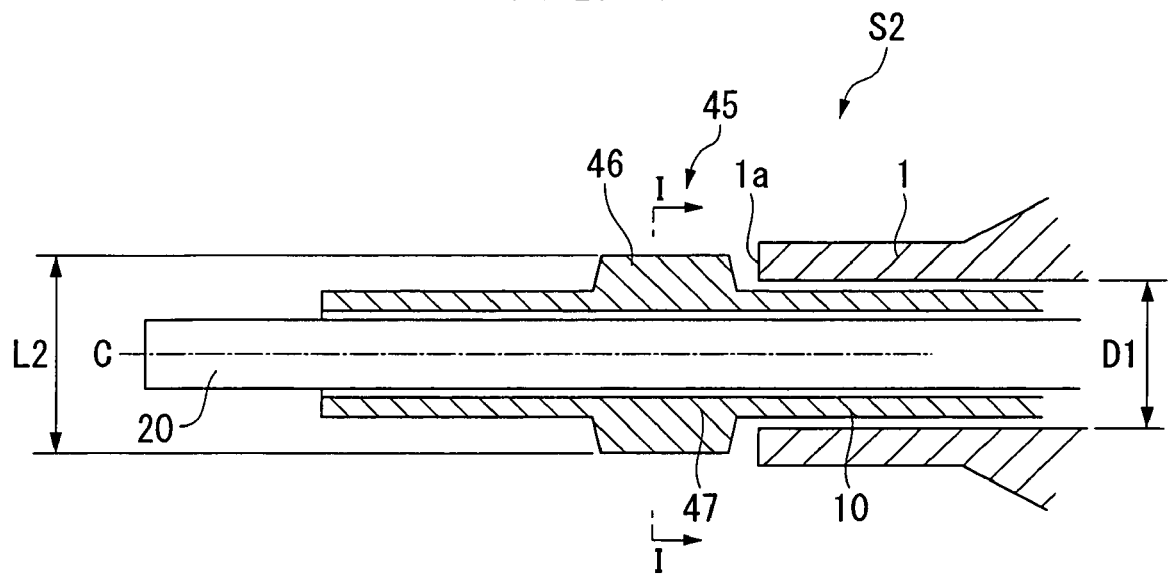
FIG. 10 is a view showing a second embodiment of a stent delivery system of the present invention, and shows a sectional surface of the head section of the guide catheter.
Figure 11:
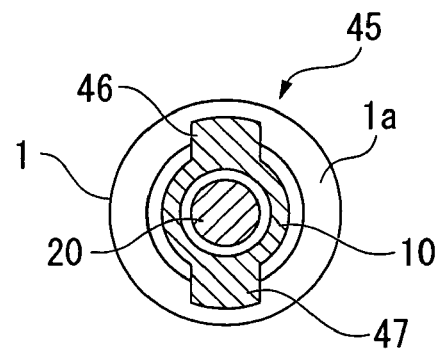
FIG. 11 is a sectional view taken along a line I-I in FIG. 10.

As shown in FIGS. 10 and 11, an engaging portion 45 is disposed on a head section of a guide catheter 10 included in the stent delivery system S2 of this embodiment. The engaging portion 45 engages with the stent 1 in a state where the guide wire 20 is inserted into the head section of the guide catheter 10, and releases the stent 1 in a state where the guide wire 20 is retracted away from the head section.

The engaging portion 45 includes two projections 46 and 47 which protrude outward along the radius of the guide catheter 10. The projections 46 and 47 are disposed so that the projection 46 is separate from the projection 47 along the radius of the guide catheter 10 across a center axis C of the guide catheter 10, and each projection is a thickness portion integrally-formed with the guide catheter 10. Further, a distance L2 from a top of the projection 46 to a top of the projection 47 is longer than the internal diameter D1 of the stent 1.

In a state where the guide wire 20 is inserted inside the guide catheter 10, the guide wire 20 supports the projections 46 and 47 from the inside of the guide catheter 10, and thereby the projections 46 and 47 are prevented from moving inward along the radius of the guide catheter 10. On the other hand, in a state where the guide wire 20 is retracted away from the guide catheter 10, the projections 46 and 47 can move inward along the radius of the guide catheter 10, because the projections 46 and 47 lose the support of the guide wire 20.

A description is given of a procedure of an operation for placing the stent in a stricture of the biliary tract using the stent delivery system S2 constructed as mentioned above. Note that because the operation to the stent 1 and the insertion of the head section of the guide catheter 10 into the stricture X is identical to the first embodiment, the description thereof is omitted.

Figure 12:
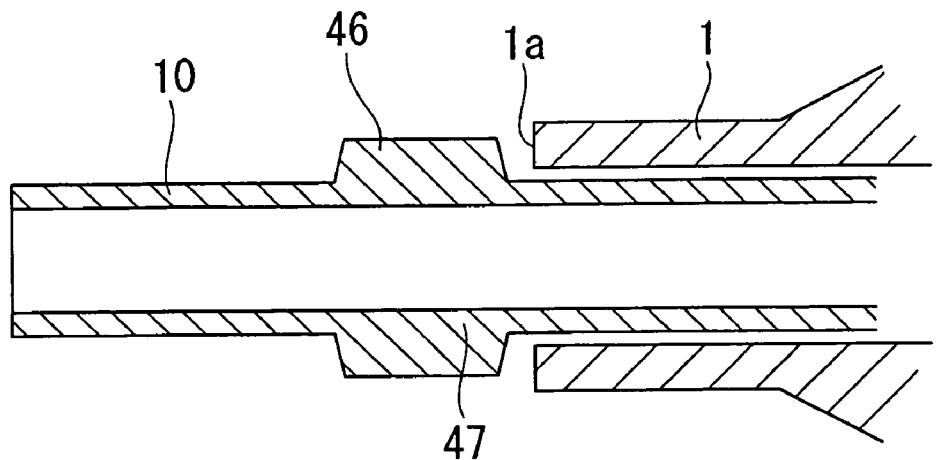
FIG. 12 is a view showing the second embodiment of the stent delivery system of the present invention, and shows a state where the guide wire is retracted.

After the stent 1 and the head section of the guide catheter 10 are inserted into the stricture X, in a state where the pusher catheter 30 is held in place, the guide wire 20 is retracted by pulling the guide wire 20 so as to be retracted away from the channel 7 of the insertion portion 6 of the endoscope. When the tip end section of the guide wire 20 is retracted to the inside of the pusher catheter 30, as shown in FIG. 12, the projections 46 and 47 can move inward along the radius of the guide catheter 10 because the guide wire 20 supporting the projections 46 and 47 from the inside of the guide catheter 10 is left.

Figure 13:
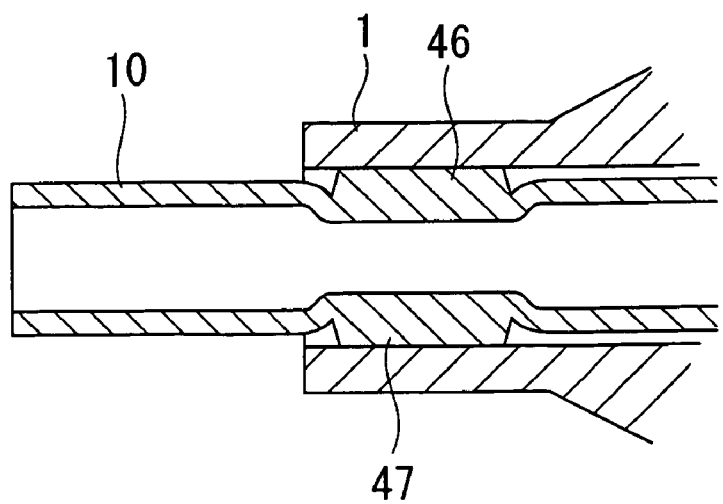
FIG. 13 is a view for depicting the procedure of the operation performed using the second embodiment of the stent delivery system of the present invention, and shows a state where the guide catheter is in the middle of being retracted.

Next, in a state where the pusher catheter 30 is held in place, the guide catheter 10 is retracted by pulling so as to be retracted away from the channel 7 of the insertion portion 6 of the endoscope (see FIG. 3). When the guide catheter 10 is pulled, each of the projections 46 and 47 contacts the end surface of the stent 1. In a state where the tip of the guide wire 20 protrudes from the tip of the guide catheter 10, the guide wire 20 supports the projection 17 from the inside of the guide catheter 10, and thereby the projections 46 and 47 are prevented from moving inward along the radius of the guide catheter 10. However, since the tip end section of the guide wire 20 is already retracted to the inside of the pusher catheter 30, when the guide catheter 10 is pulled, the projections 46 and 47 move inward along the radius of the guide catheter 10 by reaction forces acting from the end surface 1a of the stent 1. Further, as shown in FIG. 13, the tip end section of the guide catheter 10 is pulled inside the stent 1, and thereby the engaging portion 45 releases the stent 1. When the guide catheter 10 is pulled until the indicator 13 becomes exposed at the sleeve 31, the tip end section of the guide catheter 10 is retracted away from the stent 1, and then retracts to the inside of the pusher catheter 30.

Next, when the pusher catheter 30 is retracted by pulling so as to be retracted from the channel 7 of the insertion portion 6 of the endoscope (see FIG. 3), finally, only the stent 1 is placed at the interior of the biliary tract B.

According to the stent delivery system S2 constructed as mentioned above, the engaging portion 45 provided with the guide catheter 10 engages with the stent 1 at the tip of the pusher catheter 30. As a result, if the stent 1 is placed at a position which is deeper than the target position, it is possible to replace the stent 1 at the accurate position.

With the stent delivery system S2, since the basic construction thereof is substantially equal to the conventional stent delivery system, it can be applied to the endoscope used with the conventional stent delivery system. Further, it is possible to use a ready-made stent. The operator can attach any stent having a shape and material suitable for treatment to the stent delivery system and perform the procedure using the system.

Figure 14:
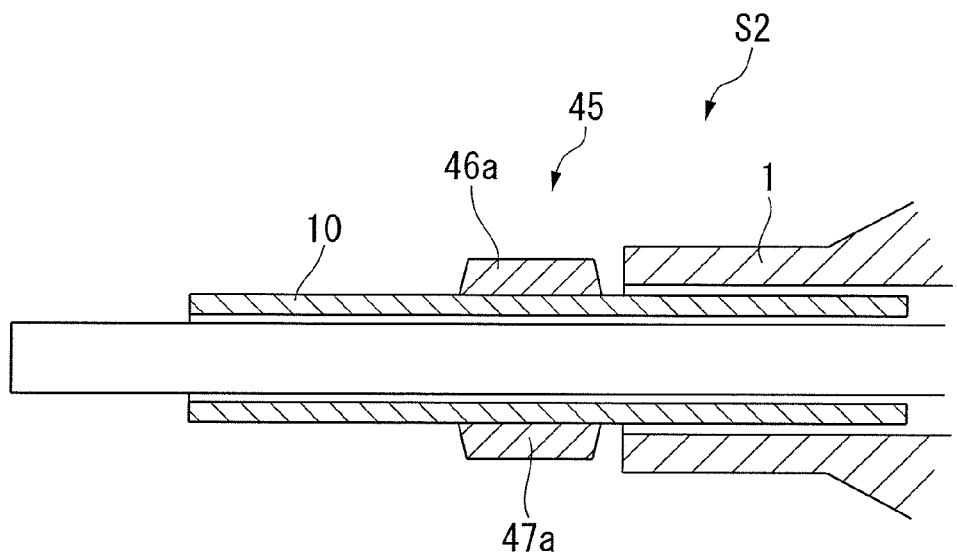
FIG. 14 is a sectional view showing a variant relating to the second embodiment of the stent delivery system of the present invention.

With this embodiment, each of the projections 46 and 47 is a thickness portion integrally-formed with the guide catheter 10. However, as shown in FIG. 14, the projections 46a and 47a may be formed by fixing other members which are different from the guide catheter 10 to the tube wall of the guide catheter 10.

Figure 15:
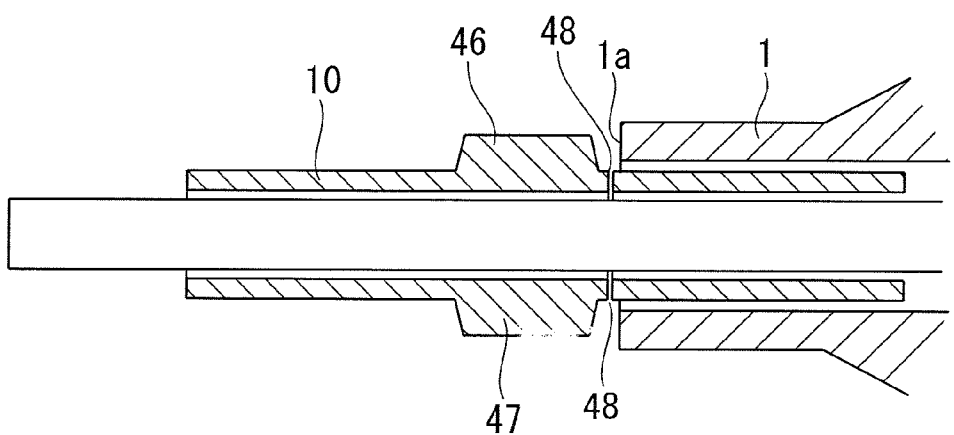
FIG. 15 is a view showing a variant of the second embodiment of the stent delivery system of the present invention, and shows a sectional surface of the head section of the guide catheter.
Figure 16:
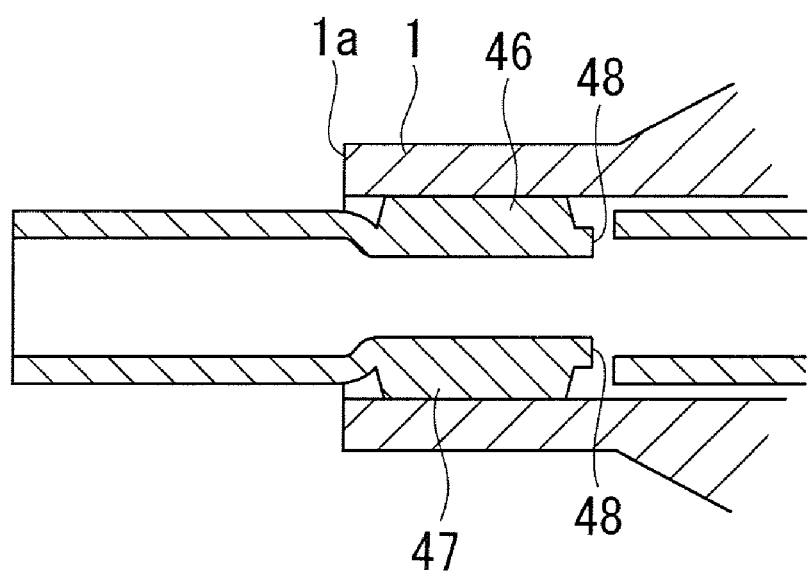
FIG. 16 is a view showing a variant of the second embodiment of the stent delivery system of the present invention, and shows a state where the guide wire is retracted.

In addition, as shown in FIG. 15, notches 48 may be formed in the tube wall of the guide catheter 10 in the vicinity of the projections 46 and 47. Therefore, since the tube wall of the guide catheter 10 becomes easy to elastically-deform, as shown in FIG. 16, when the projections 46 and 47 move inward along the radius of the guide catheter 10, forces acting on the guide catheter 10 for moving the projection 46 and 47, that is, the forces made to act on the guide catheter 10 by the operator when he pulls the guide catheter 10 are smaller than in the case in which the notches 48 are not formed in the guide catheter 10. As a result, it is possible to reduce the work burden on the operator.

Figure 17:
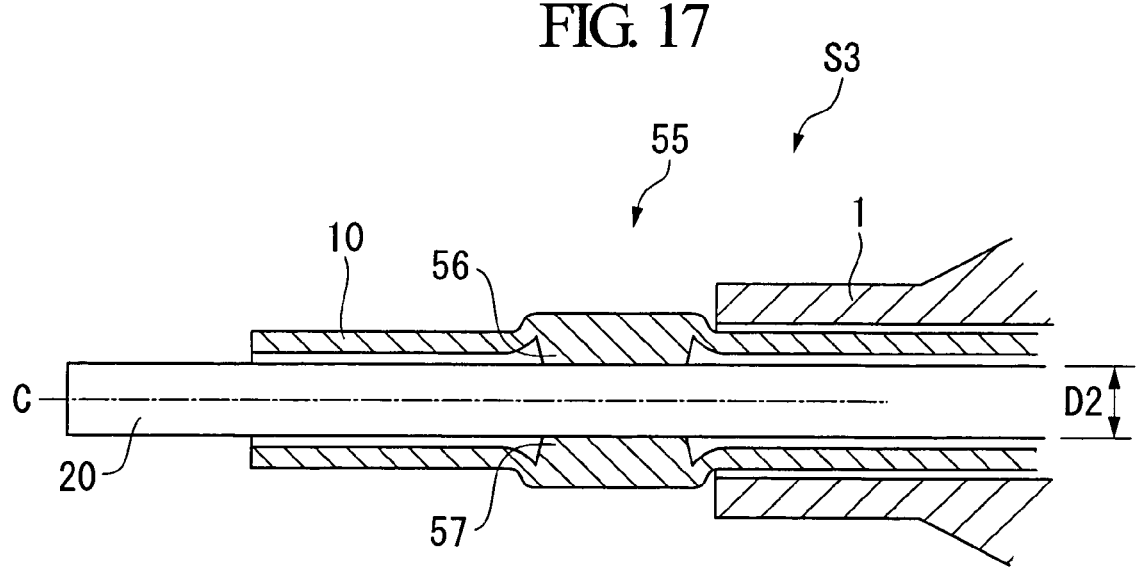
FIG. 17 is a sectional view showing a third embodiment of a stent delivery system of the present invention.
Figure 18:
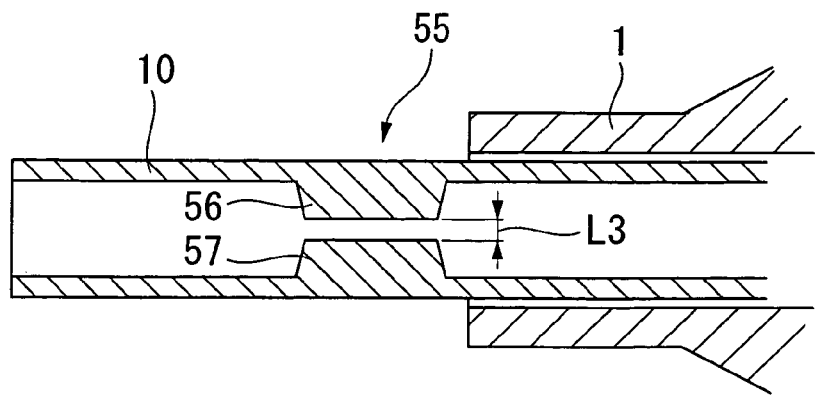
FIG. 18 is a view showing the third embodiment of the stent delivery system of the present invention, and shows a state where the guide wire is retracted.
Figure 19:
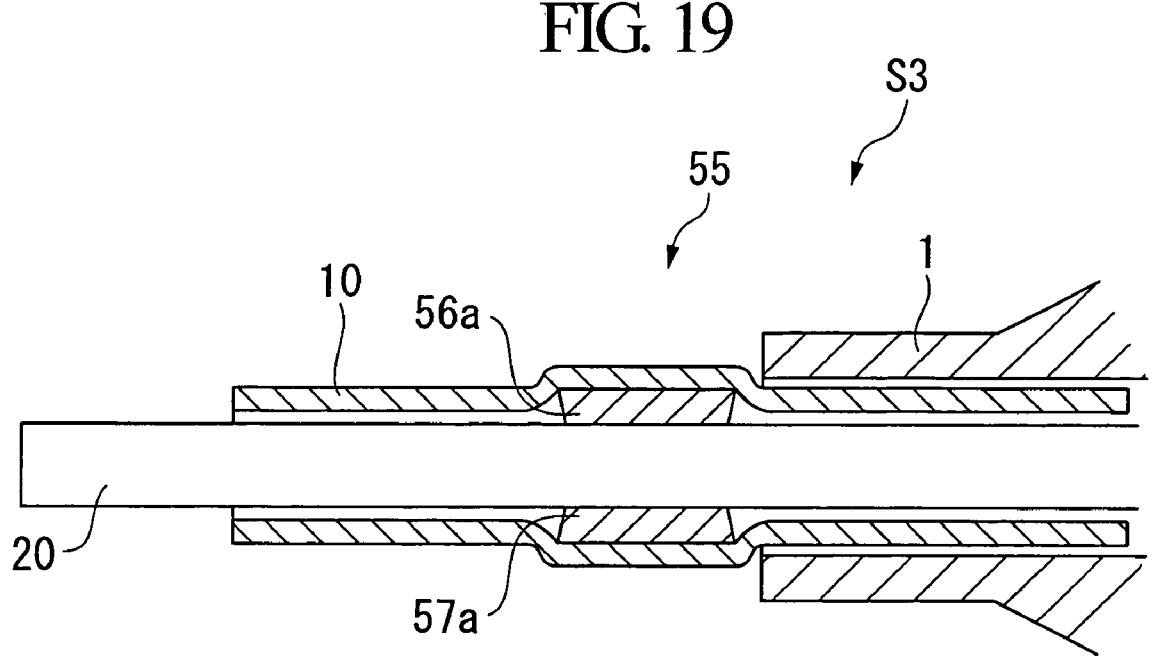
FIG. 19 is a sectional view showing a variant of the third embodiment of a stent delivery system of the present invention.

A description is given of a third embodiment of the stent delivery system of the present invention with reference to FIG. 17 through FIG. 19. Note that the same descriptive symbols are used for component elements that are the same as those used in the first and second embodiments and the descriptions thereof are omitted.

As shown in FIG. 17 and 18, an engaging portion 55 is disposed on a head section of a guide catheter 10 included in the stent delivery system S3 of this embodiment. The engaging portion 55 engages with the stent 1 in a state where the guide wire 20 is inserted into the head section of the guide catheter 10, and releases the stent 1 in a state where the guide wire 20 is retracted away from the head section.

The engaging portion 55 includes two projections 56 and 57 which protrude inward in a radius direction of the guide catheter 10. The projections 56 and 57 are disposed so that the projection 56 is separate from the projection 57 along the radius of the guide catheter 10 across a center axis C of the guide catheter 10, and each projections is a thickness portion integrally-formed with the guide catheter 10. Further, a distance L3 from a top of the projection 56 to a top of the projection 57 is shorter than an external diameter D2 of the guide wire 20.

In a state where the guide wire 20 is inserted to the inside of the guide catheter 10, the guide wire 20 is pushed in between the projections 56 and 57. In this state, the projections 56 and 57 move while elastically-deforming the tube wall of the guide catheter 10 so that the projection 56 separates from the projection 57 in the radius direction of the guide catheter 10 at a distance which is equal to the external diameter of the guide wire 20. When the projections 56 and 57 move, the outside surface of the guide catheter 10 rises, and thereby engages with the stent 1. On the other hand, in a state where the guide wire 20 is retracted away from the guide catheter 10, the projections 56 and 57 go back to an initial position, and thereby release the stent 1, because the projections 56 and 57 lose the support of the guide wire 20.

A description is given of a procedure of an operation for placing the stent at a stricture of the biliary tract using the stent delivery system S3 constructed as mentioned above. Note that because the operation of the insertion of the stent 1 and the head section of the guide catheter 10 into the stricture X is identical to the first embodiment, the description thereof is omitted.

After the stent 1 and the head section of the guide catheter 10 are inserted into the stricture X, in a state where the pusher catheter 30 is held in place, the guide wire 20 is retracted by pulling so as to be retracted away from the channel 7 of the insertion portion 6 of the endoscope. When the head section of the guide wire 20 is retracted to the inside of the pusher catheter 30, as shown in FIG. 18, the projections 56 and 57 go back to their initial positions, and thereby release the stent 1 because the guide wire 20 supporting the projections 56 and 57 from the inside of the guide catheter 10 is left.

Next, in a state where the pusher catheter 30 is held in place, the guide catheter 10 is retracted by pulling so as to be retracted away from the channel 7 of the insertion portion 6 of the endoscope. Since the projections 56 and 57 already release the stent 1, when the guide catheter 10 is pulled until the indicator 13 becomes exposed from the sleeve 31, the head section of the guide catheter 10 is retracted away from the stent 1 without causing interference with the stent 1, and then retracts to the inside of the pusher catheter 30.

Next, when the pusher catheter 30 is retracted by pulling the pusher catheter 30 so as to retract it from the channel 7 of the insertion portion 6 of the endoscope, finally, only the stent 1 is placed at the interior of the biliary tract B.

According to the stent delivery system S3 constructed as mentioned above, the engaging portion 55 provided with the guide catheter 10 engages with the stent 1 at the tip of the pusher catheter 30. As a result, if the stent 1 is placed at a position which is deeper than the target position, it is possible to replace the stent 1 at the accurate position.

With the stent delivery system S3, since the basic construction thereof is substantially equal to the conventional stent delivery system, it can be applied to the endoscope used with the conventional stent delivery system. Further, it is possible to use a current stent. The operator can attach any stent having a shape and material suitable for treatment to the stent delivery system and perform the procedure using the system.

With this embodiment, each of the projections 56 and 57 is the thickness portion integrally-formed with the guide catheter 10. However, as shown in FIG. 19, the projections 56a and 57a may be formed by fixing other members which are different from the guide catheter 10 to the tube wall of the guide catheter 10.

Similar to the second embodiment, the notches 48 may be formed in the tube wall of the guide catheter 10 in the vicinity of the projections 56 and 57.

While preferred embodiments of the invention have been described and illustrated above, it should be understood that these are examples of the invention and are not to be considered limiting. Additions, omissions, substitutions, and other modifications can be made without departing from the spirit or scope of the present invention. Accordingly, the invention is not considered to be limited by the foregoing description, and is only limited by the scope of the appended claims.

What is claimed is:

1. A guide catheter being insertable inside a stent and inside a pusher catheter which pushes the stent, and adapted for being inserted into the interior of a living body with the stent and the pusher catheter by being guided along a guide member inserted inside the guide catheter, the guide catheter comprising:

an elongated tubular main body; and an engaging portion formed at a head section of the main body so as to be integrated with the main body and to protrude outward from an outside surface of the main body, wherein, in a state where the guide member is inserted into the main body, the engaging portion is supported by the guide member from the inside thereof, thereby the engaging portion protrudes outward and contacts only a distal end of the stent put on the distal end of the pusher catheter, in a state where the guide member is retracted away from the main body, the engaging portion loses the support by the guide member from the inside of the main body, thereby the engaging portion allows release of the stent from the guide catheter.

2. The guide catheter according to claim 1, wherein
the engaging portion is supported by the guide member so as to protrude outward, and
the engaging portion shifts radially inward of the main body by losing the support of the guide member, and thereby releases the stent in the state where the guide member is retracted away from the main body.

3. The guide catheter according to claim 2, wherein
the engaging portion is provided on the inside surface of a tube wall of the guide catheter so as to protrude toward the inside of the guide catheter.

4. The guide catheter according to claim 2, wherein
the engaging portion is provided on the outside surface of a tube wall of the guide catheter so as to protrude toward the outside of the guide catheter.

5. The guide catheter according to claim 2, wherein
the engaging portion is a thickness portion integrally-formed with a tube wall of the guide catheter.

6. The guide catheter according to claim 2, wherein
the engaging portion is another member fixed to a tube wall of the guide catheter.

7. The guide catheter according to claim 1, wherein
the engaging portion is supported by the guide member so as not to move inward, and thereby engages with the stent in the state where the guide member is inserted into the main body, and further wherein
the engaging portion loses the support of the guide member, and thereby becomes movable inward in a state where the guide member is retracted away from the main body.

8. The guide catheter according to claim 7, wherein
the engaging portion is provided on the inside surface of a tube wall of the guide catheter so as to protrude toward the inside of the guide catheter.

9. The guide catheter according to claim 7, wherein
the engaging portion is provided on the outside surface of a tube wall of the guide catheter so as to protrude toward the outside of the guide catheter.

10. The guide catheter according to claim 7, wherein
the engaging portion is a thickness portion integrally-formed with a tube wall of the guide catheter.

11. The guide catheter according to claim 7, wherein
the engaging portion is another member fixed to a tube wall of the guide catheter.

12. The guide catheter according to claim 1, wherein
a notch which makes the engaging portion move with deformation of the guide catheter is formed in the main body so as to bisect a tube wall of the guide catheter.

13. A stent delivery system for placing a cylindrically-shaped stent at a desired position within a living body, the stent delivery system comprising:

a guide catheter being insertable to the inside of the stent, and adapted for being insertable into the interior of the living body with the stent by a guide member inserted inside the guide catheter; and a pusher catheter formed in a tube shape, and adapted for being insertable into the interior of the living body with the guide catheter in a state where the guide catheter is inserted inside the pusher catheter, and which is for pushing the stent along the guide catheter; wherein the guide catheter comprising;

an elongated tubular main body; and an engaging portion formed at a head section of the main body so as to be integrated with the main body and to protrude outward from an outside surface of the main body, wherein, in a state where the guide member is inserted into the main body, the engaging portion is supported by the guide member from the inside thereof, thereby the engaging portion protrudes outward and contacts only a distal tip surface of the stent, a distal end of the pusher catheter contacts only a proximal tip surface of the stent, the stent is held between the engaging portion and the distal end of the pusher catheter, and wherein, in a state where the guide member is retracted away from the main body, the engaging portion loses the support by the guide member from the inside of the main body, thereby the engaging portion allows release of the stent from the guide catheter.

14. The stent delivery system according to claim 13, wherein
the engaging portion is supported by the guide member so as to protrude outward, and
the engaging portion shifts radially inward of the main body by losing the support of the guide member, and thereby releases the stent in the state where the guide member is retracted away from the main body.

15. The stent delivery system according to claim 14, wherein
the engaging portion is provided on the inside surface of a tube wall of the guide catheter so as to protrude toward the inside of the guide catheter.

16. The stent delivery system according to claim 14, wherein
the engaging portion is provided on the outside surface of a tube wall of the guide catheter so as to protrude toward the outside of the guide catheter.

17. The stent delivery system according to claim 14, wherein
the engaging portion is a thickness portion integrally-formed with a tube wall of the guide catheter.

18. The stent delivery system according to claim 14, wherein
the engaging portion is another member fixed with a tube wall of the guide catheter.

19. The stent delivery system according to claim 13, wherein
the engaging portion is supported by the guide member so as not to move inward, and thereby engages with the stent in the state where the guide member is inserted into the main body, and further wherein
the engaging portion loses the support of the guide member, and thereby becomes movable inward in a state where the guide member is retracted away from the main body.

20. The stent delivery system according to claim 19, wherein
the engaging portion is provided on the inside surface of a tube wall of the guide catheter so as to protrude toward the inside of the guide catheter.

21. The stent delivery system according to claim 19, wherein
the engaging portion is provided on the outside surface of a tube wall of the guide catheter so as to protrude toward the outside of the guide catheter.

22. The stent delivery system according to claim 19, wherein
the engaging portion is a thickness portion integrally-formed with a tube wall of the guide catheter.

23. The stent delivery system according to claim 19, wherein
the engaging portion is another member fixed with a tube wall of the guide catheter.

24. The stent delivery system according to claim 13, wherein
a notch which makes the engaging portion move with deformation of the guide catheter is formed in the main body so as to bisect a tube wall of the guide catheter.

25. The stent delivery system according to claim 13, wherein
the stent and the pusher catheter engage with a part in which the guide member of the guide catheter is inserted, in the state where the guide member is inserted into the main body.

* * * * *